(12) United States Patent
Jang et al.

(10) Patent No.: US 11,660,009 B2
(45) Date of Patent: May 30, 2023

(54) APPARATUS AND METHOD FOR ESTIMATING BIO-INFORMATION

(71) Applicant: SAMSUNG ELECTRONICS CO., LTD., Suwon-si (KR)

(72) Inventors: Dae Geun Jang, Yongin-si (KR); Ui Kun Kwon, Hwaseong-si (KR); Chang Soon Park, Chungju-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 446 days.

(21) Appl. No.: 16/811,038

(22) Filed: Mar. 6, 2020

(65) Prior Publication Data

US 2021/0007615 A1    Jan. 14, 2021

(30) Foreign Application Priority Data

Jul. 11, 2019   (KR) .................. 10-2019-0083701

(51) Int. Cl.
| | | |
|---|---|---|
| *A61B 5/021* | (2006.01) | |
| *A61B 5/024* | (2006.01) | |
| *A61B 5/02* | (2006.01) | |
| *A61B 5/00* | (2006.01) | |

(52) U.S. Cl.
CPC ...... *A61B 5/02125* (2013.01); *A61B 5/02007* (2013.01); *A61B 5/02116* (2013.01); *A61B 5/02416* (2013.01); *A61B 5/7207* (2013.01); *A61B 2560/0223* (2013.01)

(58) Field of Classification Search
None
See application file for complete search history.

(56) References Cited

U.S. PATENT DOCUMENTS

| | | | |
|---|---|---|---|
| 8,086,301 B2 | 12/2011 | Cho et al. | |
| 8,100,835 B2 | 1/2012 | Baruch | |
| 8,548,578 B2 | 10/2013 | Matsunaga et al. | |

(Continued)

FOREIGN PATENT DOCUMENTS

| | | |
|---|---|---|
| JP | 2003-334181 A | 11/2003 |
| JP | 2012-081194 A | 4/2012 |

(Continued)

OTHER PUBLICATIONS

"Seamless Healthcare Monitoring: Advancement in Wearable, Attachable, and Invisible Devices", Tamura et al., Ed. Springer International Publishing AG 2018. (Year: 2018).*

(Continued)

*Primary Examiner* — Yi-Shan Yang
(74) *Attorney, Agent, or Firm* — Sughrue Mion, PLLC

(57) ABSTRACT

Provided is an apparatus for non-invasively estimating bio-information by analyzing a pulse waveform. The apparatus for estimating bio-information according to an aspect of the present disclosure includes a processor configured to obtain a first characteristic point from a first pulse wave signal measured by a pulse wave sensor at a calibration time, obtain a second characteristic point from a second pulse wave signal measured by the pulse wave sensor at a bio-information estimation time, based on time information of the obtained first characteristic point, and estimate the bio-information of an object based on the obtained second characteristic point.

18 Claims, 15 Drawing Sheets

(56) References Cited

U.S. PATENT DOCUMENTS

| | | | |
|---|---|---|---|
| 8,560,245 B2* | 10/2013 | Li | A61B 5/022 703/11 |
| 8,706,206 B2 | 4/2014 | Kanai et al. | |
| 2002/0147401 A1* | 10/2002 | Oka | A61B 5/02125 600/490 |
| 2004/0002659 A1* | 1/2004 | Ohama | A61B 5/02108 600/490 |
| 2008/0228089 A1 | 9/2008 | Cho et al. | |
| 2009/0076398 A1* | 3/2009 | Li | A61B 5/022 600/494 |
| 2011/0144460 A1 | 6/2011 | Oh et al. | |
| 2011/0144461 A1 | 6/2011 | Oh et al. | |
| 2011/0288424 A1 | 11/2011 | Kanai et al. | |
| 2012/0095358 A1 | 4/2012 | Matsunaga et al. | |
| 2014/0180145 A1 | 6/2014 | Kanai et al. | |
| 2017/0209055 A1* | 7/2017 | Pantelopoulos | A61B 5/7203 |
| 2018/0078215 A1 | 3/2018 | Park et al. | |
| 2018/0199822 A1* | 7/2018 | Lee | A61B 5/7275 |
| 2018/0220990 A1 | 8/2018 | Wei et al. | |
| 2019/0282106 A1* | 9/2019 | Shay | A61B 5/02125 |
| 2021/0219855 A1* | 7/2021 | Misharin | A61B 5/1128 |

FOREIGN PATENT DOCUMENTS

| | | |
|---|---|---|
| JP | WO2011052183 A1 | 3/2013 |
| KR | 10-2008-0083505 A | 9/2008 |
| KR | 10-2010-0119338 A | 11/2010 |
| KR | 10-2011-0067462 A | 6/2011 |
| KR | 10-2014-0120620 A | 10/2014 |
| KR | 10-2014-0134143 A | 11/2014 |
| KR | 10-2018-0031484 A | 3/2018 |
| WO | 2018172352 A1 | 9/2018 |

OTHER PUBLICATIONS

Ricardo Couceiro et al "Assessment of cardiovascular function from multi-Gaussian fitting of a finger photoplethysmogram" Physiological Measurement, vol. 36, 2015, (pp. 1801-1825).

Dae-Geun Jang et al. "Framework for Automatic Delineation of Second Derivative of Photoplethysmogram: A Knowledge-based Approach" Journal of Medical and Biological Engineering, vol. 34, No. 6, 2014, (pp. 547-553).

Martin C Baruch et al. "Pulse Decomposition Analysis of the digital arterial pulse during hemorrhage simulation" Nonlinear Biomedical Physics, vol. 5: 1:15, 2011, (16 pages total).

* cited by examiner

APPARATUS AND METHOD FOR ESTIMATING BIO-INFORMATION

CROSS-REFERENCE TO RELATED APPLICATION(S)

This application is based on and claims priority under 35 U.S.C. § 119 to Korean Patent Application No. 10-2019-0083701, filed on Jul. 11, 2019, in the Korean Intellectual Property Office, the disclosure of which is incorporated by reference herein in its entirety.

BACKGROUND

1. Field

The following description relates to technology for estimating bio-information by analyzing the waveform of a pulse wave signal.

2. Description of Related Art

Recently, with the aging population, soaring medical costs, and a lack of medical personnel for specialized medical services, research is being actively conducted on information technology (IT)-medical convergence technologies, in which IT technology and medical technology are combined. Particularly, monitoring of the health condition of the human body is not limited to places such as hospitals, but is expanding to mobile healthcare fields that may monitor a user's health state anywhere and anytime in daily life at home or at the office. Typical examples of bio-signals, which indicate the health condition of individuals, include an electrocardiography (ECG) signal, a photoplethysmogram (PPG) signal, an electromyography (EMG) signal, and the like, and various bio-signal sensors are being developed to measure these signals in daily life. Particularly, a PPG sensor may estimate blood pressure of a human body by analyzing the shape of pulse waves which reflect a cardiovascular state, and the like.

SUMMARY

According to an aspect of the disclosure, an apparatus for estimating bio-information may include a processor configured to obtain a first characteristic point from a first pulse wave signal measured by a pulse wave sensor at a calibration time, obtain a second characteristic point from a second pulse wave signal measured by the pulse wave sensor at a bio-information estimation time, based on time information of the obtained first characteristic point, and estimate the bio-information of an object based on the obtained second characteristic point.

The apparatus may include the pulse wave sensor including a light source configured to emit light toward the object, and a detector configured to detect light reflected by or scattered from the object.

The first pulse wave signal may be measured by the pulse wave sensor while a user is in a stable state.

The processor may perform preprocessing of at least one of removing noise from the first pulse wave signal or the second pulse wave signal, and correcting the first pulse wave signal or the second pulse wave signal.

The processor may detect the first characteristic point from at least one of the first pulse wave signal and a differential signal of the first pulse wave signal by using a characteristic point detection algorithm.

The processor may obtain a representative waveform from the first pulse wave signal, and obtain the first characteristic point from the obtained representative waveform.

The processor may obtain an amplitude, corresponding to a time of the first characteristic point, as the second characteristic point from the second pulse wave signal.

The processor may obtain a third characteristic point from at least one of the second pulse wave signal and a differential signal of the second pulse wave signal by using a characteristic point detection algorithm. In response to a reliability of the third characteristic point being less than a threshold, the processor may obtain the second characteristic point based on time information of the third characteristic point or based on the time information of the first characteristic point and the time information of the third characteristic point. In response to the reliability of the third characteristic point being greater than or equal to the threshold, the processor may obtain the third characteristic point as the second characteristic point.

The processor may obtain characteristic points at each of a plurality of times from the first pulse wave signal, and obtain a statistical value including at least one of an average value, a median value, and a mode value of the obtained characteristic points at each of the plurality of times, as the first characteristic point.

The processor may calculate the statistical value by assigning a weight to the characteristic points at each of the plurality of times.

The processor may assign the weight to the characteristic points at each of the plurality of times based on a time difference between a current time and each of the plurality of times.

The processor may determine valid characteristic points by excluding an outlier from the characteristic points at each of the plurality of times, and obtain a statistical value of the determined valid characteristic points as the first characteristic point.

The bio-information may include at least one of blood pressure, vascular compliance, cardiac output, total peripheral resistance, and vascular age.

According to an aspect of the disclosure, a method of estimating bio-information may include measuring a first pulse wave signal from an object at a calibration time, obtaining a first characteristic point from the first pulse wave signal, measuring a second pulse wave signal from the object at a bio-information estimation time, obtaining a second characteristic point from the second pulse wave signal based on time information of the obtained first characteristic point, and estimating bio-information based on the obtained second characteristic point.

The obtaining of the first characteristic point may include detecting the first characteristic point from at least one of the first pulse wave signal and a differential signal of the first pulse wave signal by using a characteristic point detection algorithm.

The obtaining of the first characteristic point may include obtaining a representative waveform from the first pulse wave signal, and obtaining the first characteristic point from the obtained representative waveform.

The obtaining of the second characteristic point may include obtaining an amplitude, corresponding to a time of the first characteristic point, as the second characteristic point from the second pulse wave signal.

The obtaining of the second characteristic point may include obtaining a third characteristic point from at least one of the second pulse wave signal and a differential signal of the second pulse wave signal by using a characteristic point detection algorithm, and calculating a reliability of the third characteristic point. In response to the reliability of the third characteristic point being less than a threshold, the method may include obtaining the second characteristic point based on time information of the third characteristic point or based on the time information of the first characteristic point and the time information of the third characteristic point. In response to the reliability of the third characteristic point being greater than or equal to the threshold, the method may include obtaining the third characteristic point as the second characteristic point.

The obtaining of the first characteristic point may include obtaining characteristic points at each of a plurality of times from the first pulse wave signal, and obtaining a statistical value of the obtained characteristic points at each of the plurality of times as the first characteristic point.

The obtaining of the first characteristic point may include calculating the statistical value by assigning a weight to the characteristic points at each of the plurality of times.

The obtaining of the first characteristic point may include assigning the weight to the characteristic points at each of the plurality of times based on a time difference between a current time and each of the plurality of times.

According to an aspect of the disclosure, an apparatus for estimating bio-information may include a pulse wave sensor configured to measure a pulse wave signal from an object, and a processor configured to obtain a second characteristic point from the pulse wave signal based on time information of first characteristic points obtained from a plurality of users, and estimate the bio-information of the object based on the obtained second characteristic point.

The apparatus may include a communication interface configured to receive the time information of the first characteristic points from an external calibration device.

The processor may detect characteristic points of each user of the plurality of users from pulse wave signals, which are measured by the pulse wave sensor from the plurality of users, and determine a statistical value including at least one of an average value, a median value, and a mode value of the time information of the characteristic points of each user to be a time of the first characteristic point.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings and the detailed description, unless otherwise described, the same drawing reference numerals may refer to the same elements, features, and structures. The relative size and depiction of these elements may be exaggerated for clarity, illustration, and convenience.

DETAILED DESCRIPTION

Figure 1:
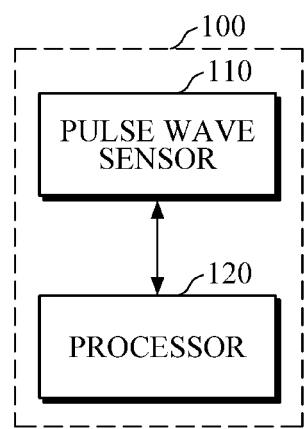
FIGS. 1 and 2 are block diagrams illustrating examples of an apparatus for estimating bio-information according to an embodiment.

Details of other embodiments are included in the following detailed description and drawings. Advantages and features of the present disclosure, and a method of achieving the same will be more clearly understood from the following embodiments described in detail with reference to the accompanying drawings. Throughout the drawings and the detailed description, unless otherwise described, the same drawing reference numerals may refer to the same elements, features, and structures.

It should be understood that, although the terms "first," "second," etc. may be used herein to describe various elements, these elements should not be limited by these terms. These terms may be used to distinguish one element from another. Any references to the singular form of a term may include the plural form of the term unless expressly stated otherwise. In addition, unless explicitly described to the contrary, an expression such as "comprising" or "including" may imply the inclusion of stated elements but not the exclusion of any other elements. Also, terms such as "part," "module," etc., may refer to a unit that performs at least one function or operation and that may be embodied as hardware, software, or a combination thereof.

Hereinafter, embodiments of an apparatus and method for estimating bio-information will be described in detail with reference to the accompanying drawings.

Figure 2:
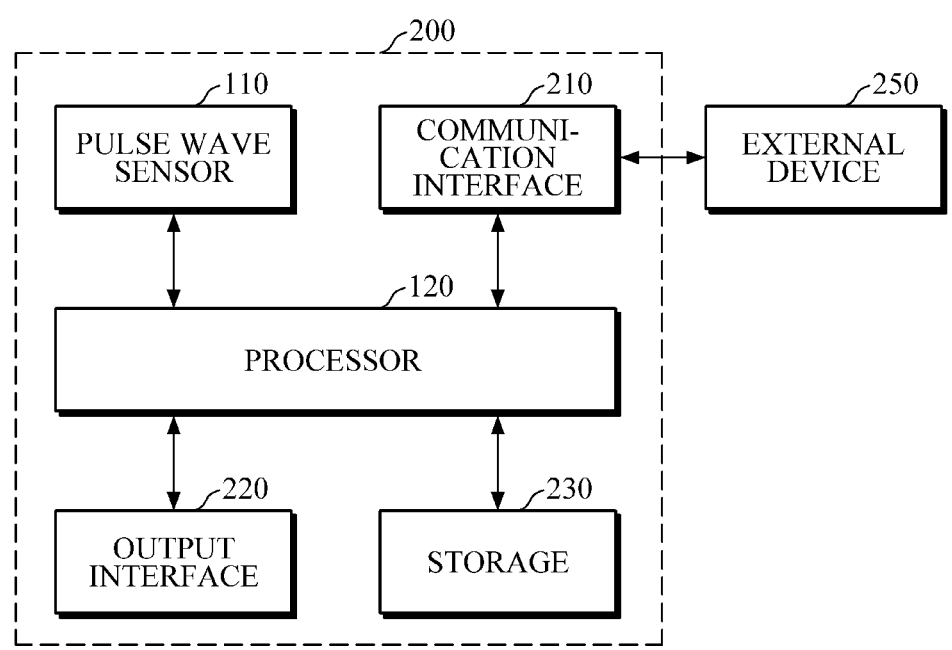

FIGS. 1 and 2 are block diagrams illustrating examples of an apparatus for estimating bio-information. The apparatus for estimating bio-information according to the embodiments of the present disclosure may be embedded in a terminal, such as a smartphone, a tablet personal computer (PC), a desktop computer, a laptop computer, and the like, or may be manufactured as an independent hardware device. In this case, the independent hardware device may be a wearable device worn on an object, and examples of the wearable device may include a wristwatch-type wearable device, a bracelet-type wearable device, a wristband-type wearable device, a ring-type wearable device, a glasses-type wearable device, a headband-type wearable device, or the like, but the wearable device is not limited thereto.

Referring to FIG. 1, the apparatus 100 for estimating bio-information includes a pulse wave sensor 110 and a processor 120.

The pulse wave sensor 110 may measure a pulse wave signal from an object. In this case, the pulse wave sensor may include a sensor which measures at least one of photoplethysmogram (PPG), impedance plethysmogram (IPG), and video plethysmogram (VPG) signals. For example, the pulse wave sensor 110, which measures the PPG signal, may include a light source configured to light toward an object and a detector for detecting light scattered by or reflected from the object. In this case, the light source may include a light emitting diode (LED), a laser diode, a phosphor, and the like. Further, the detector may include a photo diode, an image sensor, and the like, but is not limited thereto. The light source and/or the detector may be formed as an array of two or more light sources and/or detectors, and each of the light sources may emit light of different wavelengths.

The processor 120 may control various functions of the apparatus 100 for estimating bio-information. The processor 120 may be electrically connected to the pulse wave sensor 110, and may control the pulse wave sensor 110 to acquire the pulse wave signal from the object. In this case, the object may be skin tissue of the human body, and may be, for example, a body part such as the back of the hand, the wrist, fingers, and the like, at which veins or capillaries are located. However, the object is not limited thereto, and may be a body part at which arteries, such as the radial artery, are located.

In response to an occurrence of a calibration event, the processor 120 may obtain, as calibration information, a pulse wave analysis result personalized for a user and/or a general-purpose pulse wave analysis result. In this case, the calibration event may be generated in response to a user's input, at predetermined calibration intervals, or when a bio-information estimation result satisfies a predetermined calibration condition. The calibration condition may be preset based on various conditions, including a normal range of estimated bio-information values, a total number of times that the estimated bio-information values fall outside the normal range, whether the estimated bio-information values continuously fall outside the normal range by a value greater than or equal to a threshold, and the like.

For example, in response to an occurrence of the calibration event, the processor 120 may control the pulse wave sensor 110 to acquire a pulse wave signal for calibration, and may generate a pulse wave analysis result, personalized for a user, by analyzing a waveform of the acquired pulse wave signal. In this case, the pulse wave signal may be measured continuously for a predetermined period of time when a user is in a stable state.

In another example, the processor 120 may receive, from an external device, a general-purpose pulse wave analysis result, which is pre-generated using the external device by analyzing the waveform of the pulse wave signals of a plurality of users.

In yet another example, the processor 120 may control the pulse wave sensor 110 to acquire pulse wave signals for calibration from a plurality of users, and may generate a pulse wave analysis result for general use by analyzing the waveform of the pulse wave signals of the plurality of users.

In response to an occurrence of a bio-information estimation event, the processor 120 may control the pulse wave sensor 110 to acquire a pulse wave signal for estimating bio-information. In this case, the bio-information estimation event may be generated in response to a user's input, at predetermined estimation intervals, and the like. Furthermore, the processor 120 may obtain a characteristic point based on the pulse wave analysis result personalized for a user and/or the general-purpose pulse wave analysis result, and may estimate bio-information by using the obtained characteristic point. In this case, the bio-information may include blood pressure, vascular compliance, cardiac output, total peripheral resistance, vascular age, and the like, but is not limited thereto.

Referring to FIG. 2, an apparatus 200 for estimating bio-information includes a communication interface 210, an output interface 220, and a storage 230, in addition to the pulse wave sensor 110 and the processor 120.

The pulse wave sensor 110 may include one or more sensors for measuring pulse wave signals including PPG, IPG, VPG, and the like, as described above. The pulse wave sensor 110 may be electrically connected to the processor 120, and may measure pulse wave signals from a user under the control of the processor 120.

In response to a request for calibration or a request for estimating bio-information, the processor 120 may control the pulse wave sensor 110, the communication interface 210, the output interface 220, the storage 230, and the like. Further, upon controlling the communication interface 210 to receive information from an external device, the processor 120 may store the received information in the storage 230 or may output the information through the output interface 220. In addition, the processor 120 may refer to the storage 230 to obtain information required for estimating bio-information, and may estimate bio-information by using the obtained information.

The communication interface 210 may communicate with an external device 250 to transmit and receive information related to estimating bio-information. In this case, examples of the external device 250 may include a blood pressure measuring device such as a cuff-type blood pressure measuring device, a medical device related to measuring other types of bio-information, and an information processing device such as a smartphone, a tablet PC, a desktop computer, a laptop computer, and the like.

For example, the processor 120 may receive reference information for estimating blood pressure such as a cuff pressure, a bio-information estimation model, a pulse wave analysis result for general use, and the like, from the external device 250. In addition, the processor 120 may transmit the pulse wave signal measured by the pulse wave sensor 110, the pulse wave analysis result, and the bio-information estimation result which are generated by the processor 120, and the like, to the external device 250 such as a user's smartphone, a tablet PC, and the like.

The communication interface 210 may communicate with the external device 250 by using various wired or wireless communication techniques such as Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, third generation (3G) communication, fourth generation (4G) communication, fifth generation (5G) communication, and the like. However, this is merely exemplary and is not intended to be limiting.

The output interface 220 may provide a user with the pulse wave signal measured by the pulse wave sensor 110, the pulse wave analysis result and the bio-information estimation result which are processing results of the processor 120, and the like. For example, the output interface 220 may provide a user with information by various visual/non-visual methods using a visual output component (e.g., a display, and the like), an audio output component (e.g., a speaker, and the like), a haptic component configured to provide vibrations, tactile sensation, and the like), and the like.

The storage 230 may store a variety of reference information for estimating bio-information, the pulse wave signal measured by the pulse wave sensor 110, the processing results of the processor 120, and the like. In this case, the reference information may include user characteristic information including a user's age, sex, health condition, and the like, a pulse wave analysis result obtained at a calibration time, a bio-information estimation model, and the like.

The storage 230 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Figure 3A:
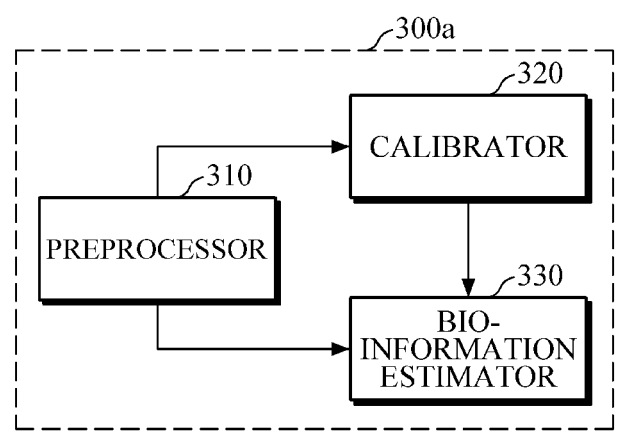
FIGS. 3A and 3B are block diagrams illustrating examples of a processor of FIGS. 1 and 2 according to an embodiment.
Figure 3B:
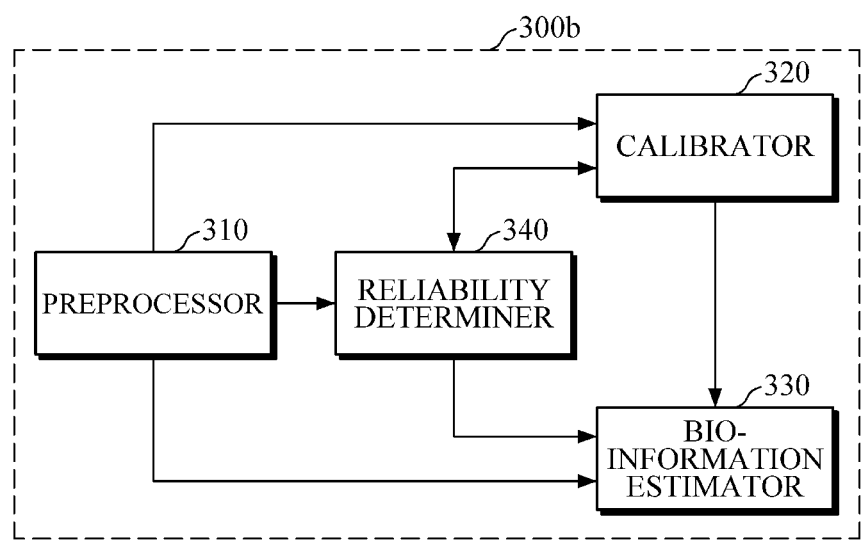
Figure 4A:
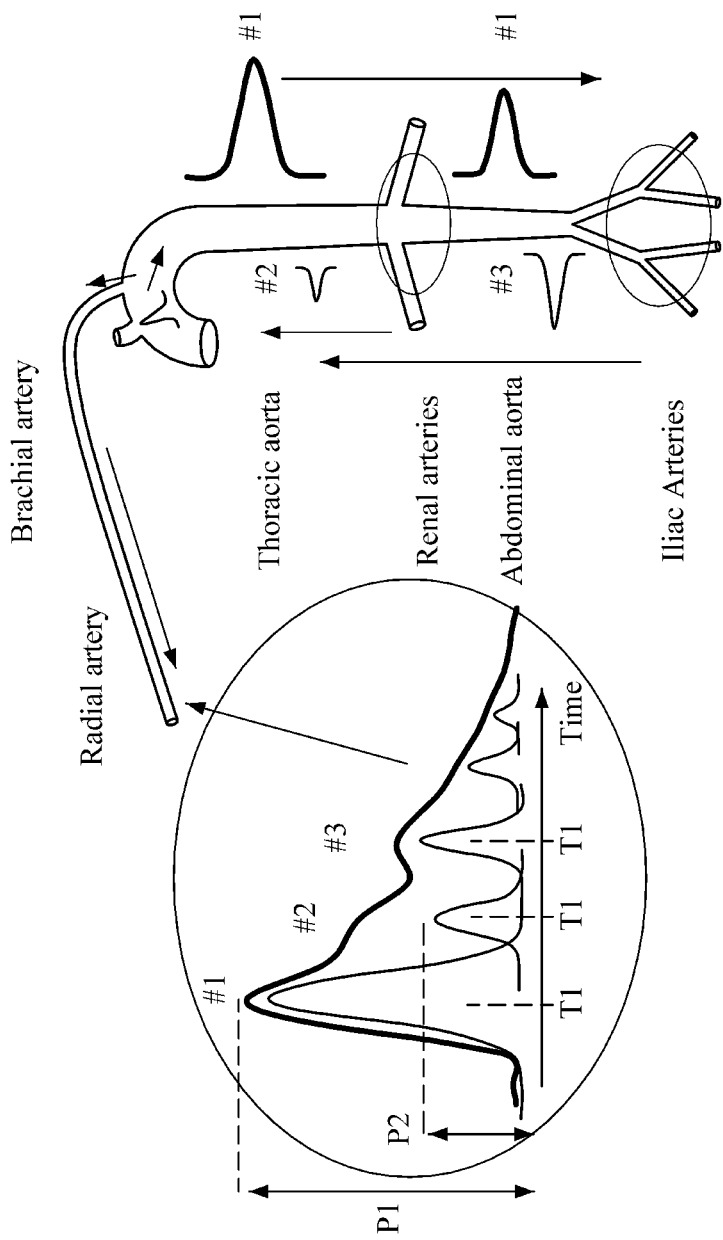
FIG. 4A is a diagram explaining phases of change of a pulse waveform according to a change of blood pressure according to an embodiment.
Figure 4B:
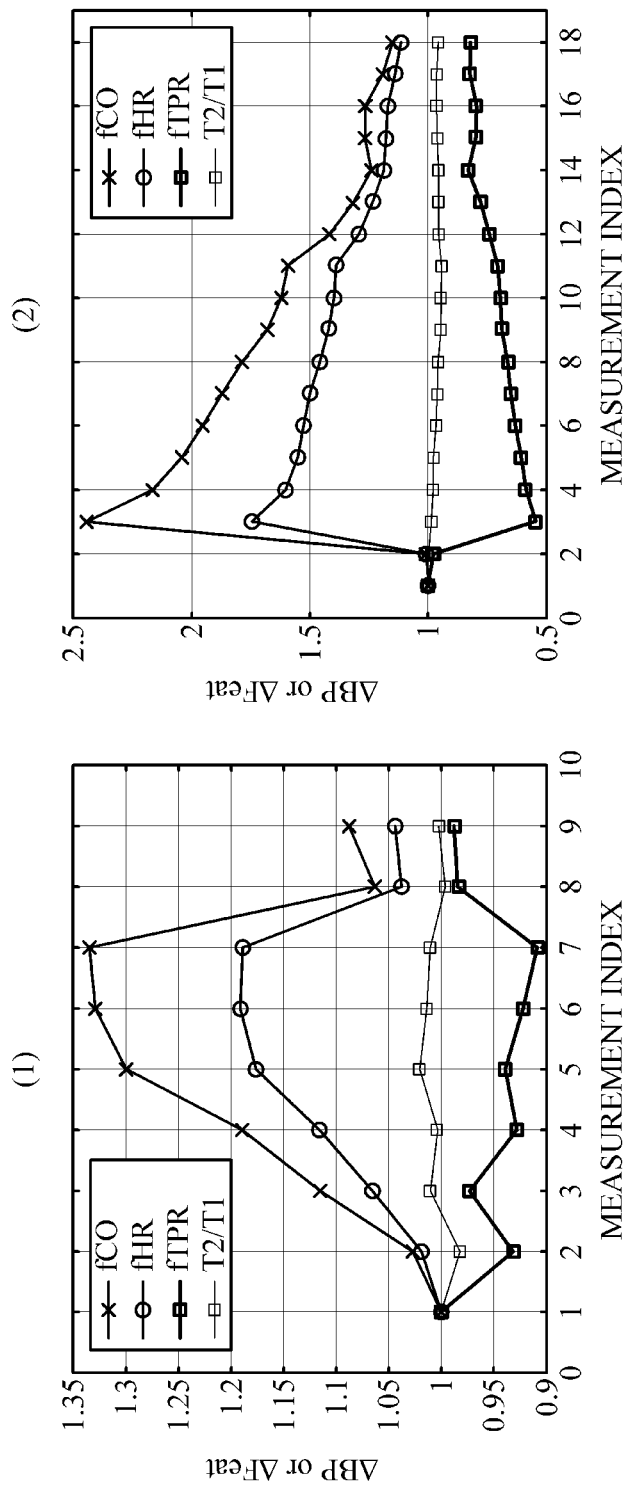
FIG. 4B is a diagram explaining a blood pressure variation according to various phases of change of blood pressure according to an embodiment.

FIGS. 3A and 3B are block diagrams illustrating examples of the processor of FIGS. 1 and 2. FIG. 4A is a diagram explaining phases of change of a pulse waveform according to a change of blood pressure. FIG. 4B is a diagram explaining a blood pressure variation according to various phases of change of blood pressure. FIGS. 5A to 5D are diagrams explaining examples of analyzing a waveform of a pulse wave signal.

Referring to FIG. 3A, a processor 300a according to an embodiment of the present disclosure includes a preprocessor 310, a calibrator 320, and a bio-information estimator 330.

The preprocessor 310 may receive a pulse wave signal from the pulse wave sensor 110, and may perform preprocessing, including removing noise from the received pulse wave signal. For example, the preprocessor 310 may perform signal correction, such as band-pass filtering between 0.4 Hz to 10 Hz, smoothing, ensemble averaging of continuously measured signals, and the like, but is not limited thereto.

Based on the pulse wave sensor 110 measuring a pulse wave signal for calibration (hereinafter referred to as a "first pulse wave signal") at a calibration time, the preprocessor 310 may obtain a representative waveform from the first pulse wave signal and may transmit the obtained representative waveform to the calibrator 320. Based on the pulse wave sensor 110 measuring a pulse wave signal for estimating bio-information (hereinafter referred to as a "second pulse wave signal") at a bio-information estimation time, the preprocessor 310 may obtain a representative waveform from the second pulse wave signal and may transmit the obtained representative waveform to the bio-information estimator 330.

Based on receiving the first pulse wave signal or the second pulse wave signal from the pulse wave sensor 110, the preprocessor 310 may divide an analysis interval of the first pulse wave signal or the second pulse wave signal into periods, to acquire a plurality of one-period signals, and may acquire any one of the plurality of one-period signals as a representative waveform, or may obtain a representative waveform by superposing two or more of the plurality of one-period signals.

For example, the preprocessor 310 may determine a one-period signal, having a greatest maximum amplitude value among the plurality of one-period signals, to be a representative waveform. Alternatively, the preprocessor 310 may determine a representative waveform by superposing one-period signals having a maximum amplitude value which is greater than or equal to a threshold value. In addition, the preprocessor 310 may extract a representative waveform based on similarities between the plurality of one-period signals. For example, based on average values of similarities between one and another one-period signals among the plurality of one-period signals, the preprocessor 310 may determine, as the representative waveform, any one one-period signal having the greatest average value, or an ensemble average of a plurality of one-period signals having an average value which is greater than or equal to a predetermined threshold value.

In this case, various similarity calculation algorithms may be used, including Euclidean distance, Manhattan Distance, Cosine Distance, Mahalanobis Distance, Jaccard Coefficient, Extended Jaccard Coefficient, Pearson's Correlation Coefficient, Spearman's Correlation Coefficient, and the like.

In an embodiment, in response to an occurrence of a calibration event, the calibrator 320 may control the pulse wave sensor 110 to acquire the first pulse wave signal. In this case, the calibrator 320 may provide, via the output interface 220, a measurement time of the first pulse wave sensor and guide information for guiding the user to remain in a stable state, so that the first pulse wave signal may be measured when the user is in a stable state.

FIG. 4A is a diagram explaining phases of change of a pulse waveform according to a change of blood pressure. Referring to FIG. 4A, a pulse wave signal is generally formed by superposing a propagation wave #1, which progresses from the heart to the distal end of the body or branching points in the blood vessels by blood ejection from the left ventricle, and reflection waves #2 and #3 which return from the distal end of the body or the branching points of the blood vessels. The propagation wave #1 is related to cardiac characteristics and the reflection waves #2 and #3 are related to vascular characteristics. As illustrated in FIG. 4A, the propagation wave #1, generated by blood ejection from the left ventricle, is mainly reflected from the renal arteries and iliac arteries, to generate the first reflection wave #2 and the second reflection wave #3. Generally, since left ventricular ejection characteristics of an individual do not change significantly, the propagation wave #1 is generated regularly, and the reflection wave #2 is also generated in an interval in which there is relatively little impedance mismatch, such that it can be assumed that there is no significant change in the characteristics of an individual.

FIG. 4B is a diagram explaining a blood pressure variation according to various phases of change of blood pressure, and showing data measured during various phases of change of cardiovascular characteristics in an individual. In FIG. 4B, (1) shows a blood pressure variation ΔBP or a variation ΔFeat in features related to blood pressure during a leg press exercise; and (2) shows a blood pressure variation ΔBP or a variation ΔFeat in features related to blood pressure during exercise on a treadmill. Here, fCO denotes a value obtained by dividing a maximum amplitude point by an area of a predetermined section of a pulse wave signal in the waveform of the pulse wave signal. Further, fHR denotes a heart rate, fTPR denotes a value obtained by dividing an amplitude value P2, corresponding to a time of the first reflection wave, by an amplitude value P1 corresponding to a time of the propagation wave.

As described above, it can be seen that even when the feature fHR related to the heart rate, the feature fCO related to the cardiac output, and the like are changed significantly, a change in time ratio T2/T2 between a time when the propagation wave #1 appears and a time when the first reflection wave #2 appears is relatively small. Accordingly, based on FIGS. 4A and 4B, it can be assumed that times T1, T2, and T3 of main characteristic points #1, #2, and #3 of the pulse waves measured from an individual have predetermined values regardless of a change in cardiovascular characteristics.

By analyzing the first pulse wave signal measured from the object as described above, the calibrator 320 may obtain calibration information personalized for a user, for example, a time value and an amplitude value of a characteristic point. Based on obtaining the calibration information, the calibrator 320 may store the information in the storage 230.

For example, the calibrator 320 may detect a first characteristic point from the first pulse wave signal, a differential signal, and/or an integral signal of the first pulse wave signal, and the like, by using a characteristic point detection algorithm. In this case, the order of differentiation or integration is not specifically limited. Further, the characteristic point detection algorithm may be defined variously according to the types of bio-signals, types of bio-information, computing performance, user characteristics such as a user's health condition, age, sex, and the like.

For example, the characteristic point detection algorithm may detect time information, related to the propagation wave, the first reflection wave, the second reflection wave, and the like, and/or amplitude information corresponding to the time information, as information of the first characteristic point.

In another example, the characteristic point detection algorithm may obtain a secondary differential signal of the first pulse wave signal, and may detect a characteristic point from the secondary differential signal. For example, the characteristic point detection algorithm may detect local minimum points from the secondary differential signal, to detect a first local minimum point as a point related to the propagation wave, and a second local minimum point and a third local minimum point as points related to the first reflection wave and the second reflection wave respectively, and may obtain a time of each of the detected points as a time of the first characteristic point. In addition, the characteristic point detection algorithm may obtain an amplitude of the first pulse wave signal, which corresponds to the time of the first characteristic point, as an amplitude of the first characteristic point.

However, the first characteristic point is not necessarily limited to points related to the propagation wave and the reflection waves, and may be obtained using a maximum amplitude point of the first pulse wave signal, a ratio between times of two or more characteristic points, a ratio between amplitudes of two or more characteristic points, or a combination thereof.

In an embodiment, in response to an occurrence of a calibration event, the calibrator 320 may obtain a first characteristic point based on a plurality of first pulse wave signals. For example, when a user is in a stable state, the calibrator 320 may control the pulse wave sensor 110 a plurality of number of times at predetermined time intervals to acquire a plurality of first pulse wave signals at a current calibration time. In another example, the calibrator 320 may control the pulse wave sensor 110 to acquire the first pulse wave signal at the current calibration time, and may acquire the first pulse wave signal at a previous time or the first characteristic point at a previous time by referring to the storage 230. In this case, the first pulse wave signal at the previous time may include a second pulse wave signal, measured for estimating blood pressure, in addition to the first pulse wave signal measured for calibration.

Based on obtaining the plurality of first pulse wave signals, the calibrator 320 may obtain characteristic points from each of the plurality of first pulse wave signals by using a characteristic point detection algorithm. The calibrator 320 may assign a weight to a statistical value, such as an average value, a median value, a mode value, and the like, of the obtained plurality of characteristic points, or to each characteristic point; and may obtain, as the first characteristic point at the current calibration time, a value obtained by linearly/non-linearly combining the weighted values. In this case, based on a time difference between the current time and each time, i.e., as a time is closer to the current time, a relatively higher weight may be assigned to the time.

By excluding an outlier from the obtained plurality of characteristic points, the calibrator 320 may combine valid characteristic points. For example, if each characteristic point is greater than a value calculated by the following Equation 1, the calibrator 320 may determine the characteristic point to be an outlier, but is not limited thereto.

$$3 \times \mathrm{median}(|f_i - \mathrm{median}(f)|) \quad \text{[Equation 1]}$$

Herein, f denotes a feature; median(f) denotes a median value of features at a plurality of times; and $f_i$ denotes a feature at each time, i being an integer greater than 1.

In an embodiment, in response to an occurrence of a calibration event, the calibrator 320 may receive a general-purpose pulse wave analysis result, e.g., time information and/or amplitude information of the first characteristic point, from the external device 250. The calibrator 320 may update the first characteristic point information, stored in the storage 230, by using the received first characteristic point information. In this case, the external device 250 may be a calibration device managed by specialized medical institutions or manufacturers of the apparatuses 100 and 200 for estimating bio-information, and the like; and may measure pulse wave signals from a plurality of users and may generate general-purpose first characteristic point information by analyzing the plurality of pulse wave signals.

In an embodiment, in response to an occurrence of a calibration event, the calibrator 320 may control the pulse wave sensor 110 to obtain the first pulse wave signals from a plurality of users. As described above, the calibrator 320 may obtain the first characteristic point from the first pulse wave signal of each user by using the characteristic point detection algorithm, and may obtain the general-purpose first characteristic point information by combining information of the first characteristic point of each user. In this case, the calibrator 320 may combine valid first characteristic points by excluding an outlier from the first characteristic points. Based on obtaining the general-purpose first characteristic point information, the calibrator 320 may provide the general-purpose first characteristic point information to the external device 250, including external apparatuses for estimating bio-information, via the communication interface 210.

The bio-information estimator 330 may monitor a bio-information estimation event; and in response to an occurrence of the bio-information estimation event, the bio-information estimator 330 may control the pulse wave sensor 110 to acquire the second pulse wave signal. Based on acquiring the second pulse wave signal, the bio-information estimator 330 may obtain a second characteristic point from the second pulse wave signal based on the first characteristic point obtained by the calibrator 320. For example, the bio-information estimator 330 may obtain the time of the first characteristic point directly as a time of the second characteristic point. Further, the bio-information estimator 330 may obtain an amplitude, corresponding to the time of the first characteristic point, as an amplitude of the second characteristic point from the second pulse wave signal.

According to the embodiments described above, the bio-information estimator 330 may obtain the characteristic point form the second pulse wave signal without using the characteristic point detection algorithm, thereby reducing the time for estimating bio-information. In addition, by using time information of the first characteristic point obtained from the first pulse wave signal measured in a stable state, robust characteristic points may be obtained even in the case where the second pulse wave signal is of poor quality, which is measured in a state in which cardiovascular characteristics are changed after high-intensity exercise and the like, for example, in the case where the second reflection wave does not appear clearly due to a fast heart rate, such that it is difficult to detect the propagation wave and the first reflection wave.

In addition, based on obtaining information of the second characteristic point, the bio-information estimator 330 may combine the information of the second characteristic point and may estimate bio-information based on the combination result. For example, the bio-information estimator 330 may combine the information by dividing an amplitude, corresponding to a time related to the first reflection wave, by an amplitude corresponding to a time related to the propagation wave in the second characteristic point of the second pulse wave signal. However, the combination is not limited thereto, and two or more time and amplitude values of the second characteristic point may be combined in various manners, including addition, subtraction, and multiplication; or a median value, a mean value, and the like of the values may also be obtained.

In addition, the bio-information estimator 330 may estimate bio-information by applying a bio-information estimation model to the combination result of the information of the second characteristic point. In this case, the bio-information estimation model may be pre-defined by using various methods such as linear/nonlinear regression analysis, neural network, deep learning, and the like.

Figure 5A:
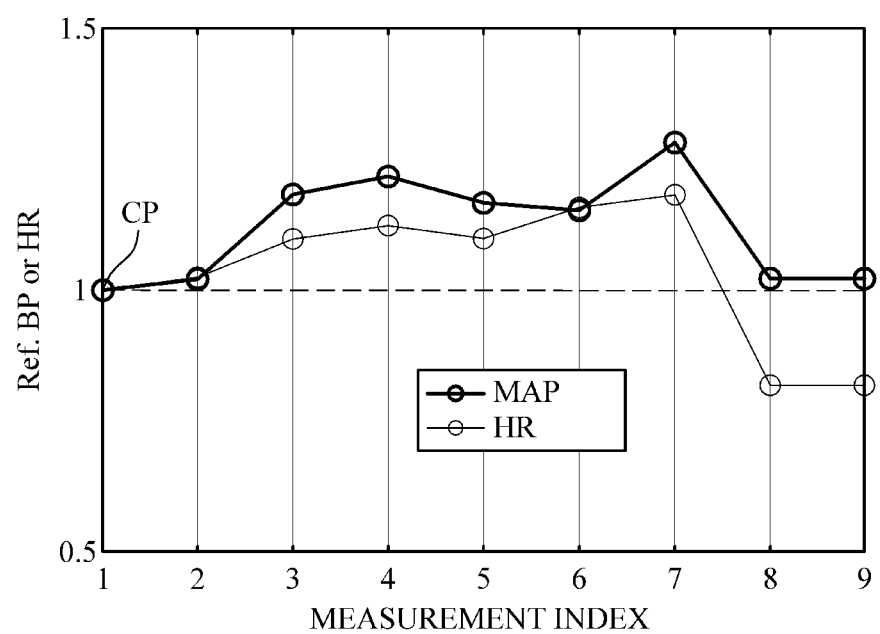
FIGS. 5A to 5D are diagrams explaining examples of analyzing a waveform of a pulse wave signal according to an embodiment.
Figure 5B:
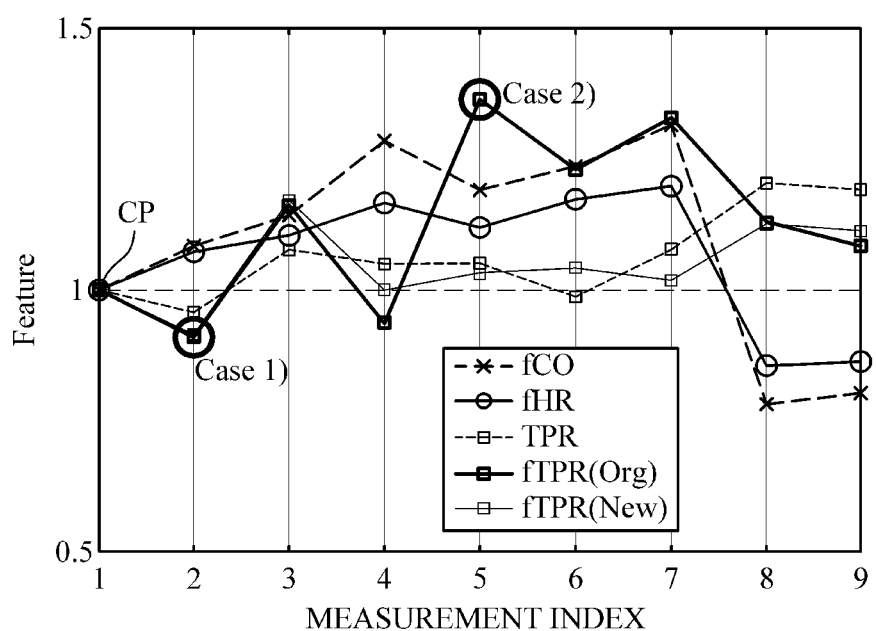
Figure 5C:
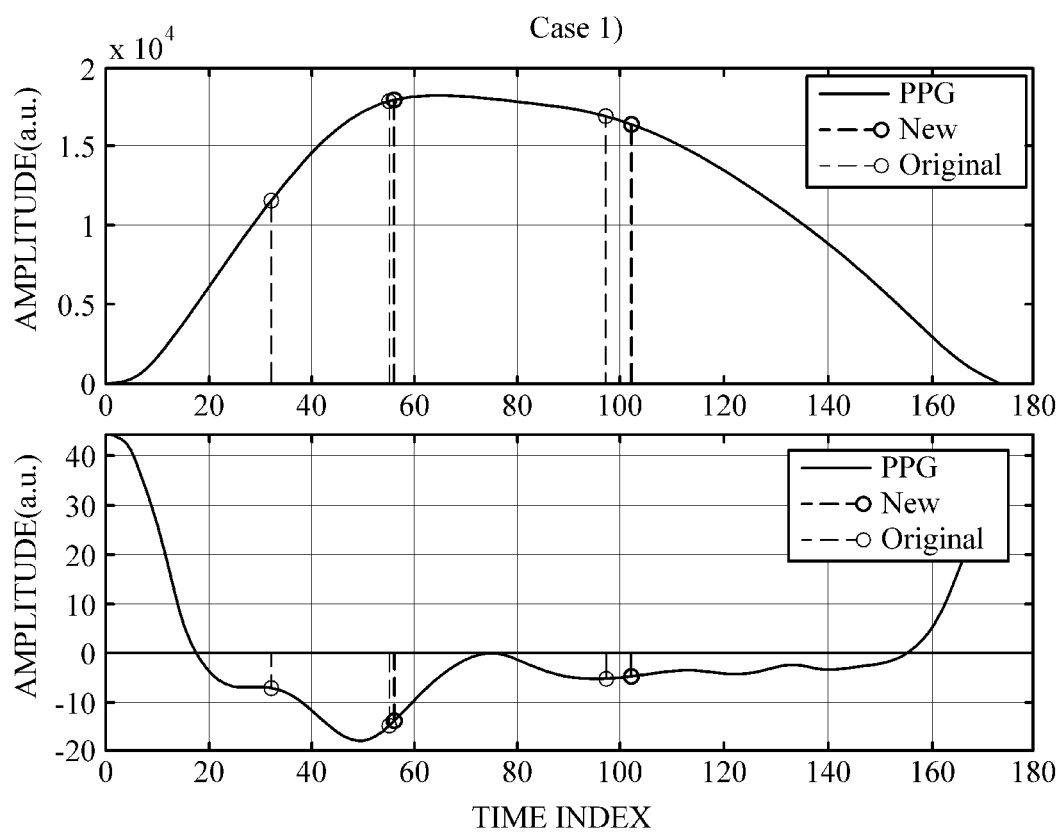
Figure 5D:
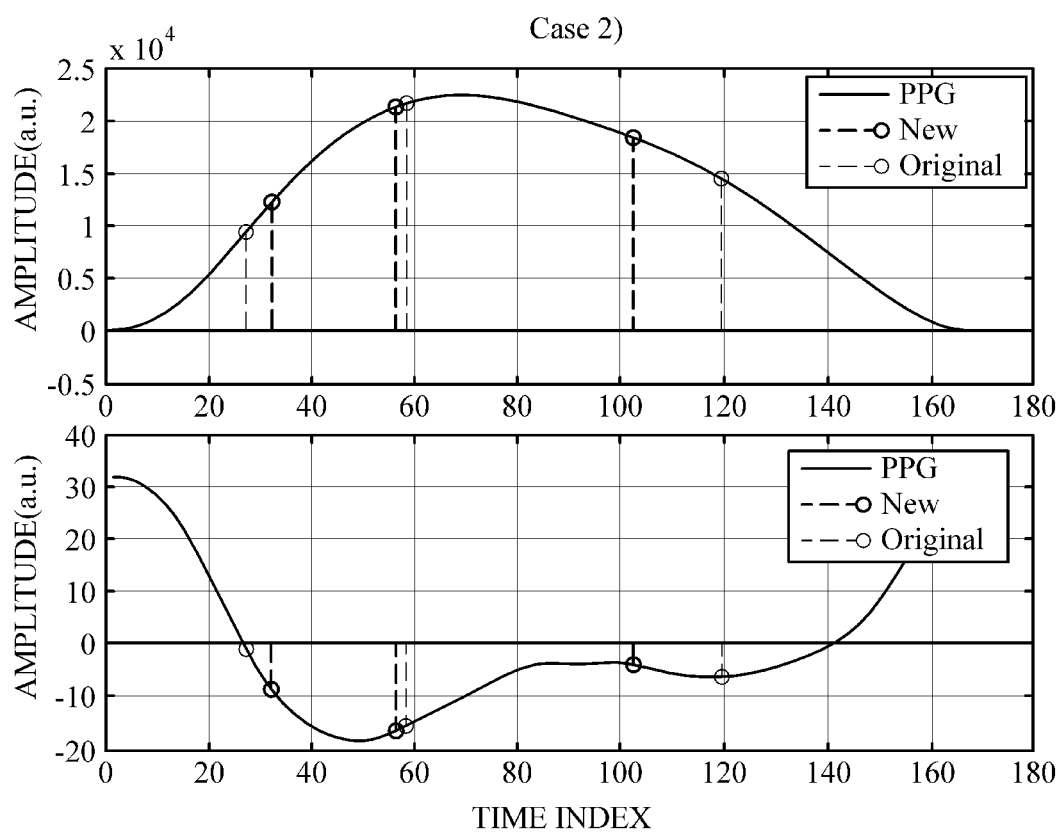

FIG. 5A is a diagram illustrating a change of reference blood pressure or heart rate with time during a leg press exercise. FIG. 5B is a diagram illustrating a feature change at each measurement time when an initial measurement time (measurement index 1) is defined as a calibration time (CP) in the experiment of FIG. 5A. FIGS. 5C and 5D are diagrams illustrating characteristic points (Original) which are obtained by a general method, and characteristic points (New) which are obtained according to the embodiment of the present disclosure, in two cases 1 and 2 of FIG. 5B.

Referring to FIGS. 5B and 5C, it can be seen that in case 1, i.e., at a time shortly after the beginning of exercise (measurement index 2), the characteristic points (Original), which are obtained by a general method, are very similar to the characteristic points (New) which are obtained according to the embodiment of the present disclosure. However, referring to FIGS. 5B and 5D, it can be seen that in case 2, i.e., at a time when a predetermined period of time elapses after the beginning of exercise (measurement index 5), there is a relatively significant difference between the characteristic points (Original), which are obtained by a general method, and the characteristic points (New) which are obtained according to the embodiment of the present disclosure. Referring to FIG. 5B, it can be seen that in case 2, a feature fTPR (New) related to total peripheral resistance, which is obtained according to the embodiment of the present disclosure, is closer to TPR than a feature fTPR (Org) obtained by a general method, and this shows that bio-information may be estimated more accurately by obtaining the characteristic points according to the embodiment of the present disclosure.

Referring back to FIG. 3B, the processor 300a according to an embodiment of the present disclosure may further include a reliability determiner 340, in addition to the preprocessor 310, the calibrator 320, and the bio-information estimator 330.

Based on the preprocessor 310 receiving the second pulse wave signal measured by the pulse wave sensor 110, the reliability determiner 340 may obtain a third characteristic point from the second pulse wave signal by using a characteristic point detection algorithm. Furthermore, the reliability determiner 340 may calculate reliability of the obtained third characteristic point, and may determine whether information of the third characteristic point is reliable information based on the calculated reliability.

For example, the reliability determiner 340 may calculate reliability of the third characteristic point based on information of the first characteristic point obtained by the calibrator 320. For example, the reliability determiner 340 may calculate the reliability of the third characteristic point based on a difference and/or a ratio between the time of the first characteristic point and the time of the third characteristic point. However, the reliability is not limited thereto.

Based on calculating the reliability of the third characteristic point, the reliability determiner 340 may compare the reliability with a predetermined threshold. If the reliability is greater than or equal to the threshold, the reliability determiner 340 may determine that information of the third characteristic point is reliable information; in contrast, if the reliability is less than the threshold, the reliability determiner 340 may determine that information of the third characteristic is unreliable information.

Based on the reliability determiner 340 determining that information of the third characteristic point is reliable information, the bio-information estimator 330 may obtain the information of the third characteristic point as information of the second characteristic point for estimating bio-information.

In contrast, based on the reliability determiner 340 determining that information of the third characteristic point is unreliable information, the bio-information estimator 330 may obtain the second characteristic point based on information of the first characteristic point and information of the third characteristic point. For example, the bio-information estimator 330 may obtain a statistical value, such as an average value, a median value, a mode value, and the like, of the time of the first characteristic point and the time of the third characteristic point, as time information of the second characteristic point. In this case, the bio-information estimator 330 may assign a relatively higher weight to the time of the first characteristic point obtained in a stable state, and then may perform combination. However, the bio-information estimator 330 is not limited thereto, and even when the reliability determiner 340 determines that information of the third characteristic point is unreliable information, the bio-information estimator 330 may obtain the second characteristic point based on the information of the third characteristic point. For example, the bio-information estimator 330 may obtain time information of the second characteristic point by using the time of the third characteristic point as it is, or may also obtain time information of the second characteristic point by using a value which is corrected by applying a correction coefficient to the time of the third characteristic point by using various methods such as addition, subtraction, multiplication, division, and the like. In this case, the correction coefficient may be determined based on a difference between reliability and the threshold.

Further, based on determining that information of the third characteristic point is unreliable information, the reliability determiner 340 may request the calibrator 320 to re-perform calibration. Criteria for determining whether to re-perform calibration, or whether to obtain the second characteristic point by using the first characteristic point and the third characteristic point as described above may be predetermined. For example, if reliability is less than a threshold, it may be determined to re-perform calibration immediately. In another example, if reliability is greater than or equal to a first threshold and less than a second threshold, it may be determined to obtain the second characteristic point by using the first characteristic point and the third characteristic point; and if the reliability is less than the first threshold, it may be determined to re-perform calibration. However, the criteria are not limited thereto.

Further, in an embodiment of the present disclosure, the reliability determiner 340 may determine reliability in response to an occurrence of a reliability determination event, so as to reduce time for detecting a characteristic point from the second pulse wave signal by using a characteristic point detection algorithm. For example, the reliability determiner 340 may determine reliability in response to a user's request, at predetermined reliability determination intervals, or based on a bio-information estimation result as described above regarding the calibrator 320. In this manner, the reliability determiner 340 may evaluate reliability of a characteristic point detection algorithm periodically or in response to a user's request.

Figure 6:
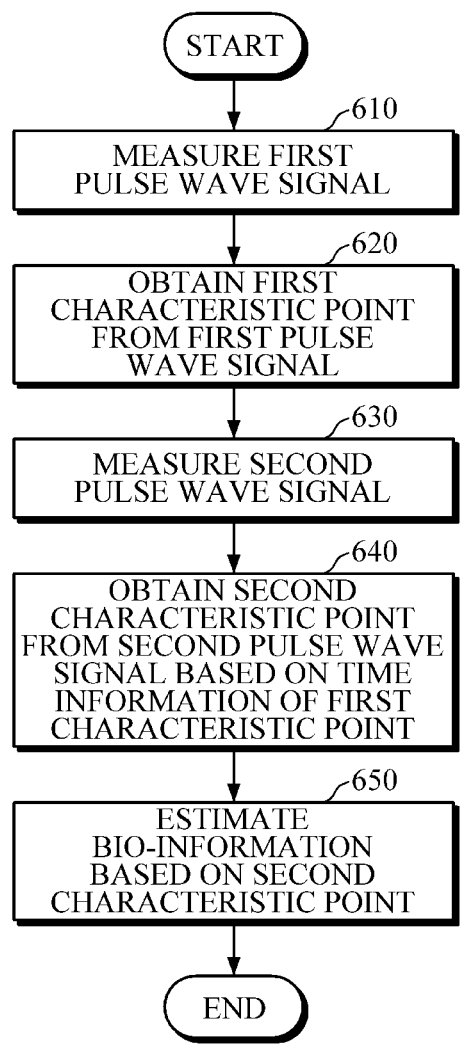
FIGS. 6 to 8 are flowcharts illustrating examples of a method of estimating bio-information according to an embodiment.

FIG. 6 is a flowchart illustrating a method of estimating bio-information according to an embodiment of the present disclosure. The method of FIG. 6 is an example of the method of estimating bio-information according to the embodiment of FIG. 1 or FIG. 2.

In response to an occurrence of a calibration event, the apparatuses 100 and 200 for estimating bio-information may drive a pulse wave sensor to measure a first pulse wave signal in operation 610.

Then, the apparatuses 100 and 200 for estimating bio-information may obtain a first characteristic point by analyzing a waveform of the first pulse wave signal in operation 620. The apparatuses 100 and 200 for estimating bio-information may obtain, as information of the first characteristic point, time and amplitude information and the like from the first pulse wave signal, a differential signal, and/or an integral signal of the first pulse wave signal, and the like, by using a pre-defined characteristic point detection algorithm. In this case, the apparatuses 100 and 200 for estimating bio-information may obtain times related to a propagation wave, a first reflection wave, and a second reflection wave as time information of the first characteristic point, but the information of the first characteristic point is not limited thereto.

Subsequently, in response to an occurrence of a bio-information estimation event, the apparatuses 100 and 200 for estimating bio-information may drive the pulse wave sensor to measure a second pulse wave signal in operation 630, and may obtain a second characteristic point from the second pulse wave signal in 640 based on the time information of the first characteristic point obtained in 620. For example, the apparatuses 100 and 200 for estimating bio-information may obtain the time of the first characteristic point, and an amplitude, corresponding to the time of the first characteristic point, in the second pulse wave signal directly as time and amplitude information of the second characteristic point.

Next, the apparatuses 100 and 200 for estimating bio-information may estimate bio-information based on the obtained second characteristic point in operation 650. The apparatuses 100 and 200 for estimating bio-information may combine the time and/or amplitude information of the second characteristic point, and may estimate bio-information by using a bio-information estimation model based on the combination result. The apparatuses 100 and 200 for estimating bio-information may provide the bio-information estimation result for a user by using various output devices such as a display, a speaker, a haptic device, and the like.

Figure 7:
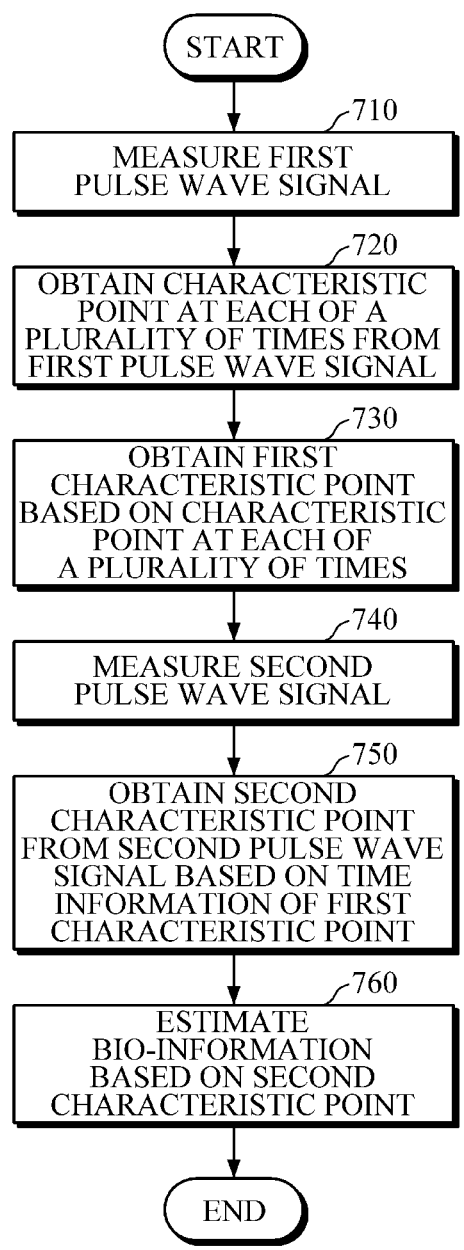

FIG. 7 is a flowchart illustrating a method of estimating bio-information according to another embodiment of the present disclosure. The method of FIG. 7 is an example of the method of estimating bio-information according to the embodiment of FIG. 1 or FIG. 2.

In response to an occurrence of a calibration event, the apparatuses 100 and 200 for estimating bio-information may drive a pulse wave sensor to measure a first pulse wave signal in operation 710. In this case, the apparatuses 100 and 200 for estimating bio-information may drive the pulse wave sensor a plurality of number of times at predetermined time intervals to acquire a plurality of first pulse wave signals. Alternatively, in addition to the first pulse wave signals measured by the pulse wave sensor at a current calibration time, the apparatuses 100 and 200 for estimating bio-information may further acquire one or more pulse wave signals obtained at previous times by referring to stored information stored in a storage.

Then, the apparatuses 100 and 200 for estimating bio-information may obtain characteristic points at each time by analyzing a waveform of the first pulse wave signal at each time in operation 720, and may obtain a first characteristic point based on the obtained characteristic points in operation 730. For example, the apparatuses 100 and 200 for estimating bio-information may obtain, as information of the first characteristic point, a statistical value such as an average value, a median value, a mode value, and the like of the characteristic points obtained from the first pulse wave signal at each time, or a value obtained by assigning a weight to each of the characteristic points and linearly/non-linearly combining the weighted characteristic points. In this case, the apparatuses 100 and 200 for estimating bio-information may exclude a characteristic point, which is an outlier, from the characteristic points obtained at each time, and may obtain the first characteristic point by combining some valid characteristic points.

Subsequently, in response to an occurrence of a bio-information estimation event, the apparatuses 100 and 200 for estimating bio-information may drive the pulse wave sensor to measure a second pulse wave signal in operation 740, and may obtain a second characteristic point from the second pulse wave signal in operation 750 based on the time information of the first characteristic point obtained in operation 730. For example, the apparatuses 100 and 200 for estimating bio-information may obtain the time of the first characteristic point, and an amplitude, corresponding to the time of the first characteristic point, in the second pulse wave signal directly as time and amplitude information of the second characteristic point.

Next, the apparatuses 100 and 200 for estimating bio-information may estimate bio-information based on the obtained second characteristic point in operation 760. The apparatuses 100 and 200 for estimating bio-information may combine the time and/or amplitude information of the second characteristic point, and may estimate bio-information by using a bio-information estimation model based on the combination result. The apparatuses 100 and 200 for estimating bio-information may provide the bio-information estimation result for a user by using various output devices such as a display, a speaker, a haptic device, and the like.

Figure 8:
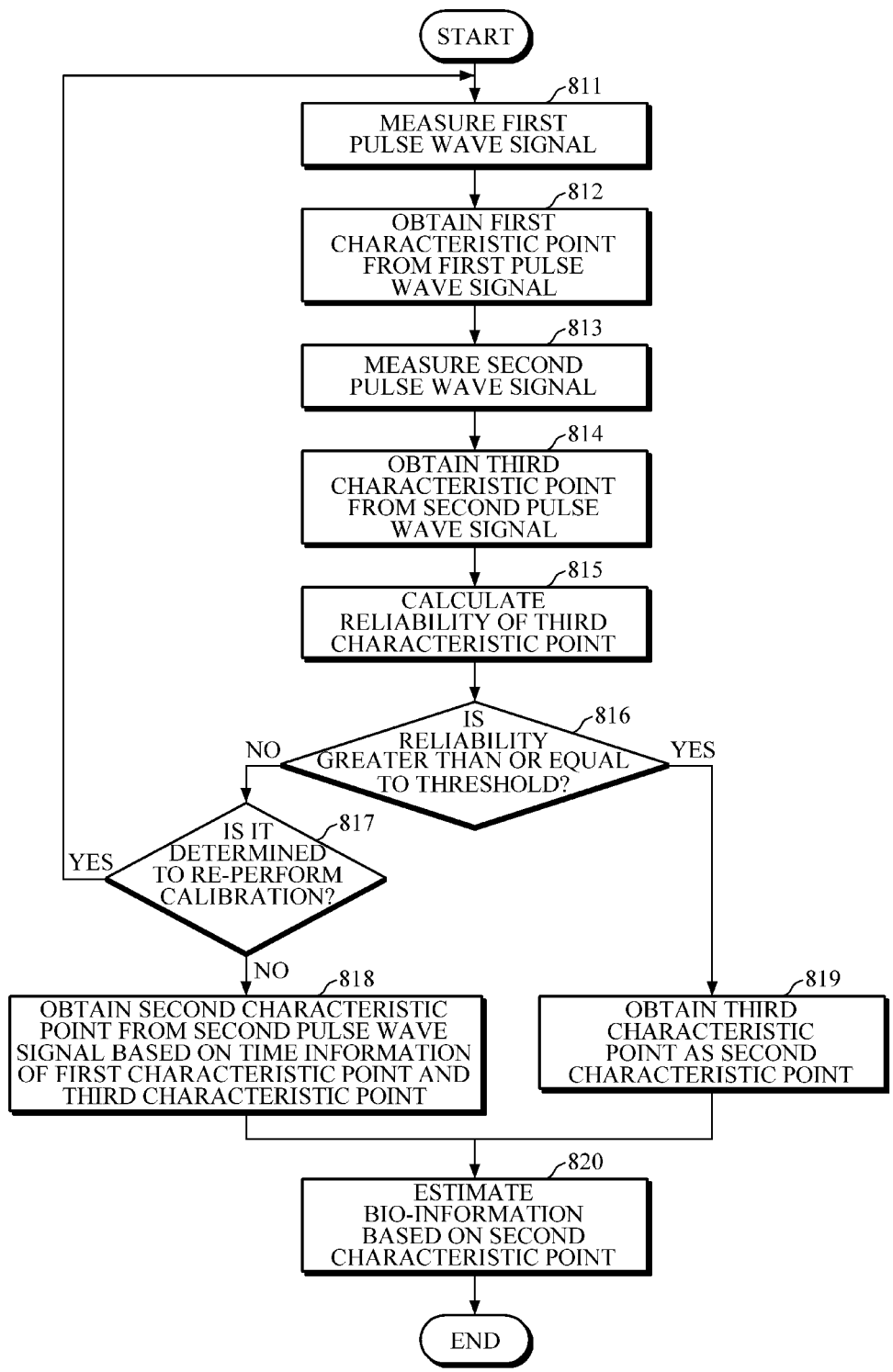

FIG. 8 is a flowchart illustrating a method of estimating bio-information according to yet another embodiment of the present disclosure. The method of FIG. 8 is an example of the method of estimating bio-information according to the embodiment of FIG. 1 or FIG. 2.

In response to an occurrence of a calibration event, the apparatuses 100 and 200 for estimating bio-information may drive a pulse wave sensor to measure a first pulse wave signal in operation 811, and may obtain a first characteristic point from the first pulse wave signal in operation 812.

Then, in response to an occurrence of a bio-information estimation event, the apparatuses 100 and 200 for estimating bio-information may drive the pulse wave sensor to measure a second pulse wave signal in operation 813, and may obtain a third characteristic point from the second pulse wave signal by using a characteristic point detection algorithm in operation 814.

Subsequently, the apparatuses 100 and 200 for estimating bio-information may calculate reliability of the third characteristic point in operation 815. In this case, the apparatuses 100 and 200 for estimating bio-information may calculate the reliability of the third characteristic point based on a difference or a ratio between the time of the first characteristic point obtained in operation 812 and the time of the third characteristic point. However, the technique to calculate reliability is not limited thereto.

Next, the apparatuses 100 and 200 for estimating bio-information may compare the reliability calculated in operation 815 with a threshold in operation 816; and if the reliability is less than the threshold, the apparatuses 100 and 200 for estimating bio-information may determine that the third characteristic point is unreliable information, and may determine whether to re-perform calibration in operation 817. In this case, determination whether to re-perform calibration may be omitted. Based on determining to re-perform calibration, the apparatuses 100 and 200 for estimating bio-information may return to operation 811 to measure the first pulse wave signal for calibration; alternatively, the apparatuses 100 and 200 for estimating bio-information may obtain a second characteristic point by combining the first characteristic point and the third characteristic point in operation 818. Based on the comparison in operation 816, if the reliability is greater than or equal to the threshold, the apparatuses 100 and 200 for estimating bio-information may determine that the third characteristic point is reliable information, and may obtain the third characteristic point as the second characteristic point in operation 819.

Then, the apparatuses 100 and 200 for estimating bio-information may estimate bio-information based on the obtained second characteristic point in operation 820. The apparatuses 100 and 200 for estimating bio-information may combine the time and/or amplitude information of the second characteristic point, and may estimate bio-information by using a bio-information estimation model based on the combination result.

Figure 9:
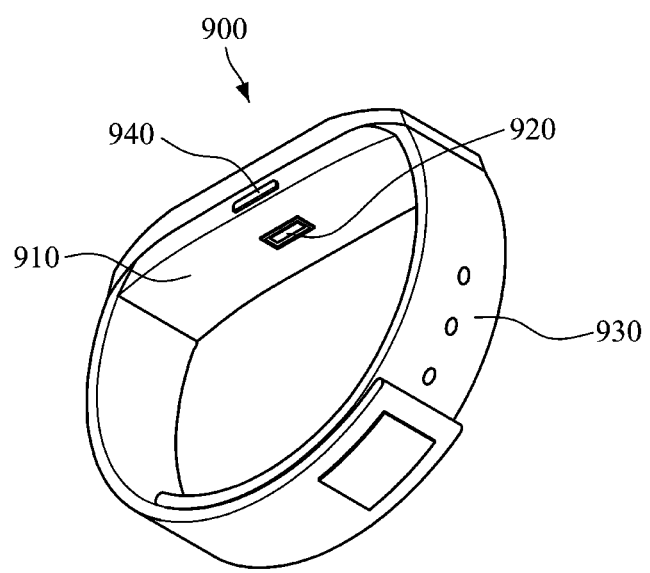
FIG. 9 is a diagram illustrating an example of a wearable device worn on a wrist according to an embodiment.

FIG. 9 is a diagram illustrating an example of a wearable device worn on a wrist. Embodiments of the apparatuses 100 and 200 for estimating bio-information described above may be mounted in a smart watch worn on a wrist or a smart band-type wearable device, but the apparatuses 100 and 200 for estimating bio-information are not limited thereto, and detailed description of various embodiments thereof may be omitted.

Referring to FIG. 9, the wearable device 900 includes a main body 910 and a strap 930.

The main body 910 may be formed to have various shapes, and may include various modules which are mounted inside or outside of the main body 910 to perform the aforementioned functions of performing calibration or estimating bio-information, as well as various other functions (e.g., a time function, an alarm function, etc.). A battery may be embedded in the main body 910 or the strap 930 to supply power to the various modules of the wearable device 900.

The strap 930 may be connected to the main body 910. The strap 930 may be flexible so as to be wrapped around a user's wrist. The strap 930 may be bent in a manner that allows the strap 930 to be detached from the user's wrist or may be formed as a band that is not detachable. Air may be injected into the strap 930 or an airbag may be included in the strap 930, so that the strap 930 may have elasticity according to a change in pressure applied to the wrist, and the change in pressure of the wrist may be transmitted to the main body 910.

The main body 910 may include a pulse wave sensor 920 for measuring a pulse wave signal. When the main body 910 is worn on a user's wrist, the pulse wave sensor 920 may be mounted on one surface of the main body 910 which contacts the user's wrist. The pulse wave sensor 920 may include a light source configured to emit light toward the wrist and a detector for detecting light scattered by or reflected from body tissue such as a skin surface, blood vessels, and the like.

In addition, a processor may be mounted in the main body 910, and may be electrically connected to the various modules of the wearable device 900 to control operations thereof.

The processor may control the pulse wave sensor 920 in response to an occurrence of a calibration event or a bio-information estimation event. The calibration event or the bio-information estimation event may be generated in response to a user's command input via a touch screen of an input component 940 or a display, at predetermined calibration intervals or bio-information estimation intervals, by monitoring a bio-information estimation result, and the like.

Based on the pulse wave sensor 920 measuring the pulse wave signal in response to the calibration event, the processor may obtain time and/or amplitude information of a characteristic point by using a characteristic point detection algorithm, and may store the obtained time and/or amplitude information as calibration information.

Further, in response to a request for estimating bio-information, the processor may control the pulse wave sensor 920 to acquire the pulse wave signal, and may obtain an amplitude, corresponding to the time included in the calibration information, as a characteristic point from the obtained pulse wave signal, and may estimate bio-information by using a bio-information estimation model based on the obtained characteristic point.

The display may be mounted on a front surface of the main body 910, and may include a touch panel for sensing a touch input. The display may receive a touch input from a user, may transmit the received touch input to the processor, and may display a processing result of the processor. For example, the display may display a bio-information estimation result, and may display additional information, such as a bio-information estimation history, a change in health condition, warning information, and the like, along with the estimation result.

A storage, which stores the processing result of the processor and a variety of information, may be mounted in the main body 910. In this case, the variety of information may include information related to estimating bio-information, as well as information related to other functions of the wearable device 900.

In addition, the main body 910 may include an input component 940 which receives a user's input and transmits the received input to the processor. The input component 940 may include a power button to input a command to turn on/off the wearable device 900.

Moreover, a communication interface, which communicates with an external device, may be mounted in the main body 910. The communication interface may transmit a bio-information estimation result to an external device, so as to output the estimation result through the external device, e.g., an output component of a user's mobile terminal, or to store the estimation result in a storage module of the external device. Furthermore, the communication interface may receive information for supporting various other functions of the wearable device and the like from the external device.

Figure 10:
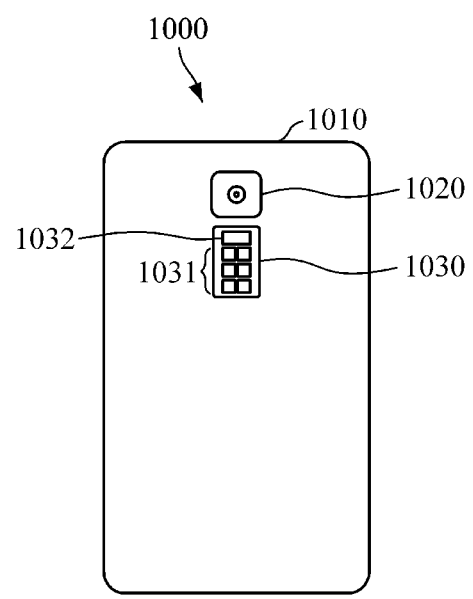
FIG. 10 is a diagram illustrating an example of a smart device according to an embodiment.

FIG. 10 is a diagram illustrating an example of a smart device, to which embodiments of the apparatuses 100 and 200 for estimating bio-information described above are applied. In this case, the smart device may be a smartphone and a tablet PC, but is not limited thereto. Detailed description of various embodiments of the apparatuses 100 and 200 for estimating bio-information described above may be omitted.

Referring to FIG. 10, the smart device 1000 may include a main body 1010 and a pulse wave sensor 1030 mounted on one surface of the main body 1010. The pulse wave sensor 1030 may include one or more light sources 1031 and a detector 1032. As described above, the pulse wave sensor 1030 may be mounted on a rear surface of the main body 1010, but is not limited thereto, and may be configured in combination with a fingerprint sensor or a touch panel mounted on a front surface of the main body 1010.

A display may be mounted on a front surface of the main body 1010. The display may visually display a bio-information estimation result and the like. The display may include a touch panel, and may receive information input via the touch panel and transmit the received information to the processor.

Moreover, an image sensor 1020 may be mounted in the main body 1010. When a user's finger approaches the pulse wave sensor 1030 to measure a pulse wave signal, the image sensor 1020 may capture an image of the finger and may transmit the captured image to the processor. In this case, based on the image of the finger, the processor may identify a relative position of the finger with respect to an actual position of the pulse wave sensor 1030, and may provide the relative position of the finger to the user through the display, so as to guide a user to accurately contact the pulse wave sensor 1030 with the finger.

The processor may obtain calibration information and may estimate bio-information by using the pulse wave signal measured by the pulse wave sensor 1030, which is described above in detail, such that description thereof may be omitted.

The present disclosure can be realized as computer-readable code stored on a non-transitory computer-readable medium. The computer-readable medium may be any type of recording device in which data is stored in a computer-readable manner.

Examples of the computer-readable medium include a ROM, a RAM, a CD-ROM, a magnetic tape, a floppy disc, an optical data storage, and a carrier wave (e.g., data transmission through the Internet). The computer-readable medium may be distributed over a plurality of computer systems connected to a network so that a computer-readable code is written thereto and executed therefrom in a decentralized manner. Functional programs, code, and code segments needed for realizing the present disclosure can be deduced by one of ordinary skill in the art.

The present disclosure has been described herein with regard to various embodiments. However, it will be obvious to those skilled in the art that various changes and modifications can be made without departing from the scope of the present disclosure. Thus, it is clear that the above-described embodiments are illustrative in all aspects and are not intended to limit the present disclosure.

What is claimed is:

1. An apparatus for estimating bio-information comprising:
   a pulse wave sensor configured to measure a pulse wave signal based on a detected light; and
   a processor configured to:
      obtain, by applying a characteristic point detection algorithm to a first pulse wave signal, a first characteristic point from the first pulse wave signal measured by the pulse wave sensor at a calibration time, the first pulse wave signal being measured by the pulse wave sensor while a user is in a non-movement state and the first characteristic point including a time value;
      obtain a second characteristic point from a second pulse wave signal measured by the pulse wave sensor at a bio-information estimation time after the calibration time, based on the time value of the obtained first characteristic point, the second characteristic point including at least one of a time value and an amplitude value, wherein the processor is configured to obtain the second characteristic point without applying the characteristic point detection algorithm to the second pulse wave signal by:
         obtaining a time value of the second pulse wave signal corresponding to the time value of the first characteristic point as the time value of the second characteristic point; and
         obtaining an amplitude value of the second pulse wave signal corresponding to the time value of the second characteristic point as the amplitude value of the second characteristic point; and
      estimate the bio-information of an object based on the at least one of the time value and the amplitude value of the obtained second characteristic point.

2. The apparatus of claim 1, wherein the processor is further configured to:
   perform preprocessing of at least one of removing noise from the first pulse wave signal or the second pulse wave signal, and correcting the first pulse wave signal or the second pulse wave signal.

3. The apparatus of claim 1, wherein the processor is further configured to:
   detect the first characteristic point from at least one of the first pulse wave signal and a differential signal of the first pulse wave signal by using the characteristic point detection algorithm.

4. The apparatus of claim 1, wherein the processor is further configured to:
obtain a representative waveform from the first pulse wave signal; and
obtain the first characteristic point from the obtained representative waveform.

5. The apparatus of claim 1, wherein the processor is further configured to:
obtain characteristic points at each of a plurality of times from the first pulse wave signal; and
obtain a statistical value including at least one of an average value, a median value, and a mode value of the obtained characteristic points at each of the plurality of times, as the first characteristic point.

6. The apparatus of claim 5, wherein the processor is further configured to:
calculate the statistical value by assigning a weight to the characteristic points at each of the plurality of times.

7. The apparatus of claim 6, wherein the processor is further configured to:
assign the weight to the characteristic points at each of the plurality of times based on a time difference between the calibration time and each of the plurality of times.

8. The apparatus of claim 5, wherein the processor is further configured to:
determine valid characteristic points by excluding an outlier from the characteristic points at each of the plurality of times; and
obtain a statistical value of the determined valid characteristic points as the first characteristic point.

9. The apparatus of claim 1, wherein the bio-information comprises at least one of blood pressure, vascular compliance, cardiac output, total peripheral resistance, and vascular age.

10. A method of estimating bio-information, the method comprising:
measuring a first pulse wave signal from an object at a calibration time;
obtaining, by applying a characteristic point detection algorithm to the first pulse wave signal, a first characteristic point from the first pulse wave signal, the first pulse wave signal being measured while a user is in a non-movement state and the first characteristic point including a time value;
measuring a second pulse wave signal from the object at a bio-information estimation time after the calibration time;
obtaining a second characteristic point from the second pulse wave signal based on the time value of the obtained first characteristic point, the second characteristic point including at least one of a time value and an amplitude value, wherein the obtaining the second characteristic point is performed without applying the characteristic point detection algorithm to the second pulse wave signal by:
obtaining a time value of the second pulse wave signal corresponding to the time value of the first characteristic point as the time value of the second characteristic point; and
obtaining an amplitude value of the second pulse wave signal corresponding to the time value of the second characteristic point as the amplitude value of the second characteristic point; and
estimating bio-information based on the at least one of the time value and the amplitude value of the obtained second characteristic point.

11. The method of claim 10, wherein the obtaining of the first characteristic point comprises detecting the first characteristic point from at least one of the first pulse wave signal and a differential signal of the first pulse wave signal by using the characteristic point detection algorithm.

12. The method of claim 10, wherein the obtaining of the first characteristic point comprises obtaining a representative waveform from the first pulse wave signal, and obtaining the first characteristic point from the obtained representative waveform.

13. The method of claim 10, wherein the obtaining of the first characteristic point comprises obtaining characteristic points at each of a plurality of times from the first pulse wave signal, and obtaining a statistical value of the obtained characteristic points at each of the plurality of times as the first characteristic point.

14. The method of claim 13, wherein the obtaining of the first characteristic point comprises calculating the statistical value by assigning a weight to the characteristic points at each of the plurality of times.

15. The method of claim 14, wherein the obtaining of the first characteristic point comprises assigning the weight to the characteristic points at each of the plurality of times based on a time difference between a current time and each of the plurality of times.

16. An apparatus for estimating bio-information, the apparatus comprising:
a pulse wave sensor configured to measure a pulse wave signal from an object; and
a processor configured to:
obtain, by applying a characteristic point detection algorithm to first pulse wave signals, first characteristic points being obtained from a plurality of users while the plurality of users are in a non-movement state; and
obtain a second characteristic point from a second pulse wave signal based on time information of the first characteristic points, the second characteristic point including at least one of a time value and an amplitude value, wherein the processor is configured to obtain the second characteristic point without applying the characteristic point detection algorithm to the second pulse wave signal by:
obtaining a time value of the pulse wave signal corresponding to a time value of the first characteristic points as the time value of the second characteristic point; and
obtaining an amplitude value of the pulse wave signal corresponding to the time value of the second characteristic point as the amplitude value of the second characteristic point; and
estimate the bio-information of the object based on the at least one of a time value and an amplitude value of the obtained second characteristic point.

17. The apparatus of claim 16, further comprising:
a communication interface configured to receive the time information of the first characteristic points from an external calibration device.

18. The apparatus of claim 16, wherein the processor is further configured to:
detect characteristic points of each of the plurality of users from pulse wave signals, which are measured by the pulse wave sensor from the plurality of users; and
determine a statistical value including at least one of an average value, a median value, and a mode value of the time information of the characteristic points of each of the plurality of users to be a time of a first characteristic point.

\* \* \* \* \*